(12) United States Patent
Renga et al.

(10) Patent No.: US 9,212,141 B2
(45) Date of Patent: Dec. 15, 2015

(54) PROCESS FOR THE PREPARATION OF 4-AMINO-5-FLUORO-3-CHLORO-6-(SUBSTITUTED)PICOLINATES

(71) Applicants: James M. Renga, Indianapolis, IN (US); Gregory T. Whiteker, Carmel, IN (US); Peter L. Johnson, Indianapolis, IN (US); Christopher Galliford, Indianapolis, IN (US)

(72) Inventors: James M. Renga, Indianapolis, IN (US); Gregory T. Whiteker, Carmel, IN (US); Peter L. Johnson, Indianapolis, IN (US); Christopher Galliford, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 43 days.

(21) Appl. No.: 14/104,197

(22) Filed: Dec. 12, 2013

(65) Prior Publication Data
US 2014/0171653 A1  Jun. 19, 2014

Related U.S. Application Data

(60) Provisional application No. 61/736,835, filed on Dec. 13, 2012.

(51) Int. Cl.
*C07D 213/08* (2006.01)
*C07D 213/72* (2006.01)

(52) U.S. Cl.
CPC .................................. *C07D 213/72* (2013.01)

(58) Field of Classification Search
CPC ........................... C07D 213/04; C07D 213/12
USPC .......................................................... 546/250
See application file for complete search history.

(56) References Cited

U.S. PATENT DOCUMENTS

| 6,784,137 | B2 | 8/2004 | Balko et al. |
| 7,314,849 | B2 | 1/2008 | Balko et al. |
| 7,432,227 | B2 | 10/2008 | Balko et al. |

*Primary Examiner* — Nizal Chandrakumar
(74) *Attorney, Agent, or Firm* — Robert Chang

(57) ABSTRACT

4-Amino-5-fluoro-3-chloro-6-(substituted)picolinates are prepared from trifluoroacetic acid, p-methoxyaniline, a 3,3-dialkoxyprop-1-yne and a substituted methylene amine by a series of steps.

1 Claim, No Drawings

PROCESS FOR THE PREPARATION OF 4-AMINO-5-FLUORO-3-CHLORO-6-(SUBSTITUTED)PICOLINATES

CROSS REFERENCE TO RELATED APPLICATIONS

This application claims the benefit of U.S. Provisional Patent Application Ser. No. 61/736,835 filed Dec. 13, 2012, the disclosure of which is expressly incorporated herein by reference.

FIELD

Provided herein are processes for the preparation of 4-amino-5-fluoro-3-halo-6-(substituted)picolinates. More particularly, provided herein are processes for the preparation of 4-amino-5-fluoro-3-chloro-6-(substituted)picolinates from a non-pyridine source.

BACKGROUND

U.S. Pat. Nos. 6,784,137 B2 and 7,314,849 B2 describe inter alia certain 4-amino-3-chloro-5-fluoro-6-(aryl)picolinate compounds and their use as herbicides. U.S. Pat. No. 7,432,227 B2 describes inter alia certain 4-amino-3-chloro-5-fluoro-6-(alkyl)picolinate compounds and their use as herbicides. Each of these patents describes the manufacture of 4-amino-3-chloro-5-fluoropicolinate starting materials by fluorination of the corresponding 5-unsubstituted pyridines with 1-(chloromethyl)-4-fluoro-1,4-diazoniabicyclo[2.2.2]octane bis(tetrafluoroborate). Each of these patents also describes the manufacture of 6-(aryl)-4-aminopicolinates from coupling reactions involving picolines having either a facile leaving group or a metal derivative in the 6-position of the picoline ring. It would be advantageous to produce 4-amino-5-fluoro-3-chloro-6-(substituted)picolinates without having to rely on metal-assisted couplings. It would be advantageous to produce 4-amino-5-fluoro-3-chloro-6-(substituted)picolinates efficiently and in high yield from a non-pyridine source. It would also be advantageous to produce 4-amino-5-fluoro-3-chloro-6-(substituted)picolinates without having to rely on direct fluorination of the 5-position of the pyridine ring with an expensive fluorinating agent like 1-(chloromethyl)-4-fluoro-1,4-diazoniabicyclo[2.2.2]octane bis(tetrafluoroborate).

SUMMARY

Provided herein are processes for the preparation of 4-amino-5-fluoro-3-chloro-6-(substituted)picolinates from a non-pyridine source without a metal assisted coupling and without fluorination with an expensive fluorinating agent like 1-(chloromethyl)-4-fluoro-1,4-diazoniabicyclo[2.2.2]octane bis(tetrafluoroborate). More particularly, provided herein are processes for the preparation of a 4-amino-5-fluoro-3-chloro-6-(substituted)picolinate of the Formula I

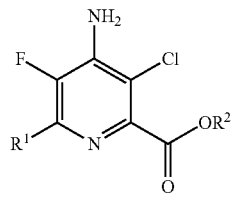

wherein
R$^1$ represents C$_1$-C$_4$ alkyl, cyclopropyl, C$_2$-C$_4$ alkenyl or phenyl substituted with from 1 to 4 substituents independently selected from halogen, C$_1$-C$_4$ alkyl, C$_1$-C$_4$ haloalkyl, C$_1$-C$_4$ alkoxy or C$_1$-C$_4$ haloalkoxy, and
R$^2$ represents C$_1$-C$_{12}$ alkyl or an unsubstituted or substituted C$_7$-C$_{11}$ arylalkyl, which comprises the following steps:

a) contacting trifluoroacetic acid with p-methoxyaniline in the presence of a triarylphosphine and a trialkylamine base in carbon tetrachloride solvent to produce an acetimidoyl chloride of Formula A

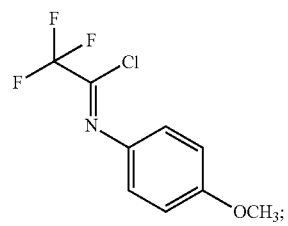

b) contacting the acetimidoyl chloride of Formula A with a 3,3-dialkoxyprop-1-yne (Formula B)

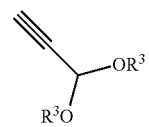

wherein R$^3$ represents C$_1$-C$_4$ alkyl, in the presence of copper (I) iodide, an alkali metal iodide and an alkali metal phosphate in a polar aprotic solvent to produce an (imino)pent-2-yne dialkyl acetal of Formula C

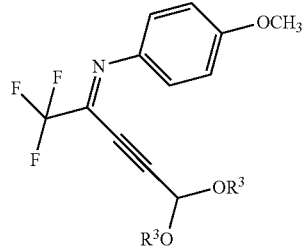

wherein R$^3$ is as previously defined;

c) cyclizing the (imino)pent-2-yne dialkyl acetal of Formula C with an amine of Formula D

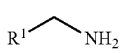

D wherein R¹ is as previously defined,
in the presence of an inorganic alkali metal base in a polar aprotic solvent at a temperature from about ambient to about 100° C. to produce a 4-(4-methoxyphenyl)amino-5-fluoro-6-(substituted)pyridine-2-dialkyl acetal of Formula E

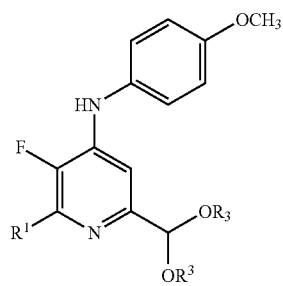

E wherein R¹ and R³ are as previously defined;

d) chlorinating the 4-(4-methoxyphenyl)amino-5-fluoro-6-(substituted)pyridine-2-dialkyl acetal of Formula E with 1,3-dichloro-5,5-dimethylimidazolidine-2,4-dione (Formula F)

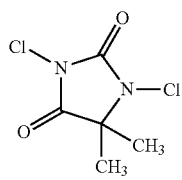

F in a polar solvent to produce the protected 4-amino-5-fluoro-3-chloro-6-(substituted)pyridine-2-dialkyl acetal of the Formula G

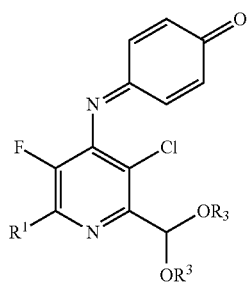

G wherein R¹ and R³ are as previously defined;

e) deprotecting and hydrolyzing the protected 4-amino-5-fluoro-3-chloro-6-(substituted)pyridine-2-dialkyl acetal of the Formula G with a mineral acid in a polar solvent to produce the 4-amino-5-fluoro-3-chloro-6-(substituted)picolinaldehyde of the Formula H

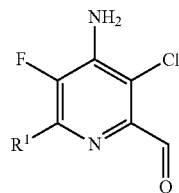

H wherein R¹ is as previously defined;

f) oxidizing the 4-amino-5-fluoro-3-chloro-6-(substituted)picolinaldehyde of the Formula H with an alkali metal chlorite in the presence of an inorganic acid and a hypochlorous acid scavenger in an aqueous alcoholic solvent to produce a 4-amino-5-fluoro-3-chloro-6-(substituted)picolinic acid of the Formula J

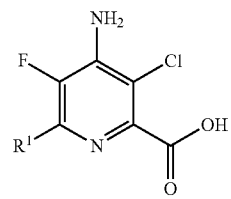

J wherein R¹ is as previously defined; and g) esterifying the 4-amino-5-fluoro-3-chloro-6-(substituted)picolinic acid of the Formula J with a compound of the formula

R²X wherein

X represents OH, Cl, Br, or I, and

R² is as previously defined to produce a 4-amino-5-fluoro-3-chloro-6-(substituted)picolinate of Formula I.

Another embodiment is a compound of Formula C

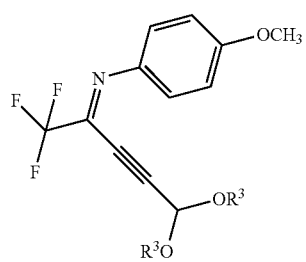

C wherein R³ represents $C_1$-$C_4$ alkyl.

Another embodiment is a compound of Formula E

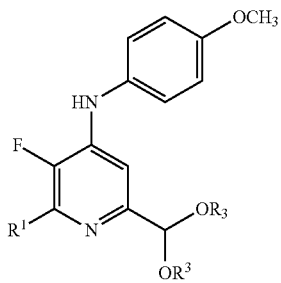

wherein
R¹ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and
R³ represents $C_1$-$C_4$ alkyl.

Another embodiment is a compound of Formula G

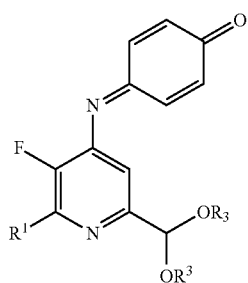

wherein
R¹ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy, and
R³ represents $C_1$-$C_4$ alkyl.

Another embodiment is a compound of Formula H

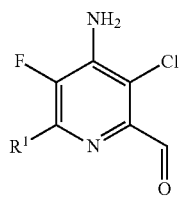

wherein
R¹ represents $C_1$-$C_4$ alkyl, cyclopropyl, $C_2$-$C_4$ alkenyl or phenyl substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy.

DETAILED DESCRIPTION

The terms "alkyl" and "alkenyl," as well as derivative terms such as "alkoxy," as used herein, include within their scope straight chain and branched chain moieties.

The term "arylalkyl," as used herein, refers to a phenyl substituted alkyl group having a total of 7 to 11 carbon atoms, such as benzyl (—$CH_2C_6H_5$), 2-methylnaphthyl (—$CH_2C_{10}H_7$) and 1- or 2-phenethyl (—$CH_2CH_2C_6H_5$ or —$CH(CH_3)C_6H_5$). The phenyl group may itself be unsubstituted or substituted with one or more substituents independently selected from halogen, nitro, cyano, $C_1$-$C_6$ alkyl, $C_1$-$C_6$ alkoxy, halogenated $C_1$-$C_6$ alkyl, halogenated $C_1$-$C_6$ alkoxy, $C_1$-$C_6$ alkylthio, C(O)O$C_1$-$C_6$ alkyl, or where two adjacent substituents are taken together as —O(CH$_2$)$_n$O— wherein n=1 or 2, provided that the substituents are sterically compatible and the rules of chemical bonding and strain energy are satisfied.

Unless specifically limited otherwise, the term "halogen," as well as derivative terms such as "halo," refers to fluorine, chlorine, bromine and iodine.

The phenyl groups substituted with from 1 to 4 substituents independently selected from halogen, $C_1$-$C_4$ alkyl, $C_1$-$C_4$ haloalkyl, $C_1$-$C_4$ alkoxy or $C_1$-$C_4$ haloalkoxy may be of any orientation, but 4-substituted phenyl, 2,4-disubstituted phenyl, 2,3,4-trisubstituted phenyl, 2,4,5-trisubstituted phenyl, and 2,3,4,6-tetrasubstituted phenyl isomers are preferred.

4-Amino-5-fluoro-3-chloro-6-(substituted)picolinates are prepared from trifluoroacetic acid, p-methoxyaniline, a 3,3-dialkoxyprop-1-yne and a substituted methylene amine by a series of steps.

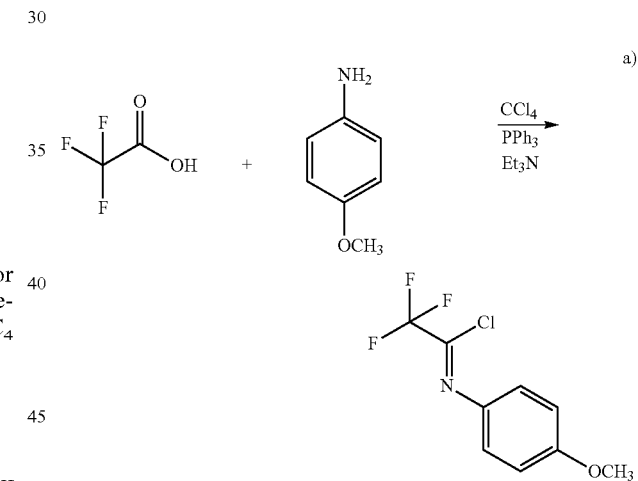

a)

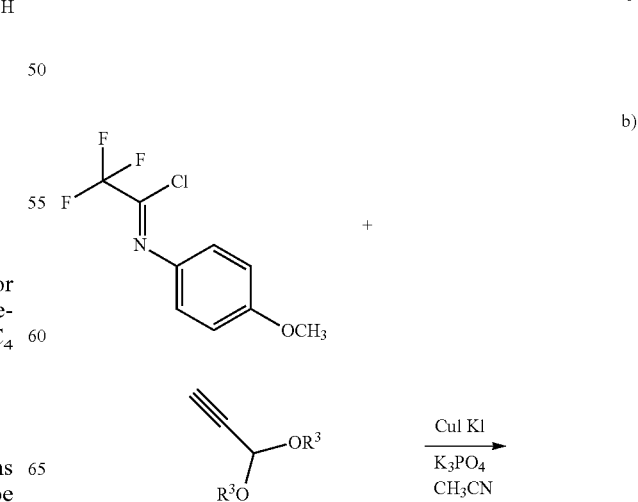

b)

7
-continued
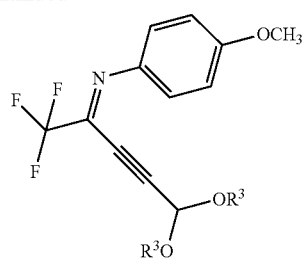
5
c)
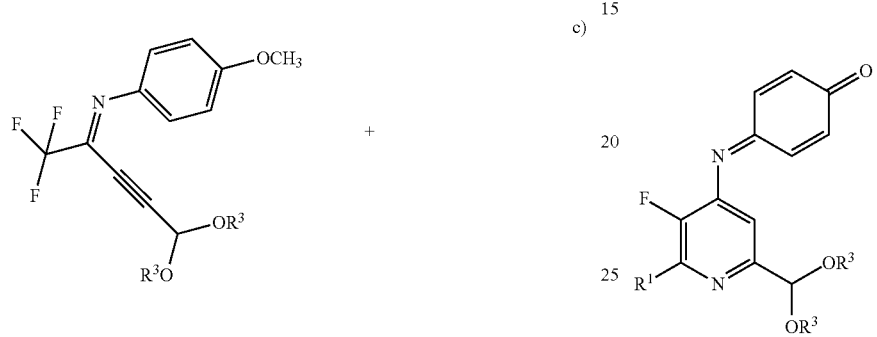
R¹CH₂NH₂ →
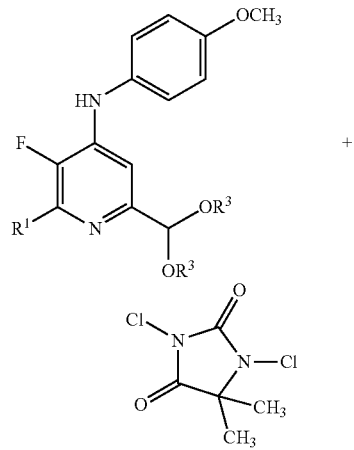
8
-continued
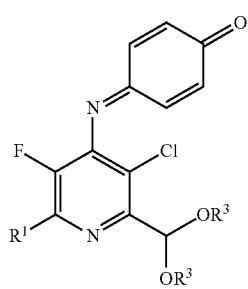
e)
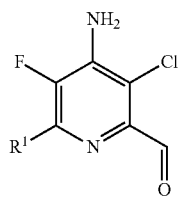
H⁺/H₂O
f)
oxid.
g)
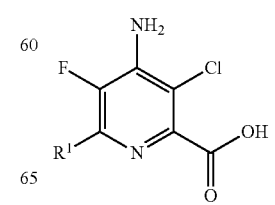
R²X →

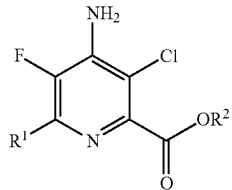

In step a), trifluoroacetic acid is reacted with p-methoxyaniline and carbon tetrachloride in the presence of a triarylphosphine and a trialkylamine base to produce 2,2,2-trifluoro-N-(4-methoxyphenyl)acetimidoyl chloride. While one equivalent of p-methoxyaniline is required for each equivalent of trifluoroacetic acid, it is often convenient to use an excess of the aniline, typically a 10 to 20% excess. A similar excess of trialkylamine base is also preferred. It is often convenient to use a much larger excess of triarylphosphine, typically in the range of a 2 to 4 fold excess. Carbon tetrachloride, while serving as a reactant, is also conveniently used as a solvent for the initial reaction. The reaction is exothermic and it is convenient to control the exotherm by external cooling and the controlled addition of a carbon tetrachloride solution of p-methoxyaniline to a mixture of trifluoroacetic acid, trialkylamine and triarylphosphine in carbon tetrachloride. After the initial exotherm subsides, the reaction mixture is generally heated to reflux until the conversion is complete.

In a typical reaction, a mixture of about 3 equivalents of triphenylphosphine and trifluoroacetic acid in carbon tetrachloride is cooled to about 0° C. in an ice bath and a 20% excess of triethylamine is added. With continued cooling, about a 20% excess of p-methoxyaniline in carbon tetrachloride is slowly added. After completion of the addition, the mixture is heated to about 70° C. for several hours. After cooling, the reaction mixture is extracted with hexane and the solvent evaporated to provide crude 2,2,2-trifluoro-N-(4-methoxyphenyl)acetimidoyl chloride.

In step b), the 2,2,2-trifluoro-N-(4-methoxyphenyl)acetimidoyl chloride is coupled with a 3,3-dialkoxyprop-1-yne in the presence of copper (I) iodide, an alkali metal iodide and an alkali metal phosphate in a polar aprotic solvent to produce an N-(5,5-dialkoxy-1,1,1-trifluoropent-3-yn-2-ylidene)-4-methoxyaniline. While one equivalent of 3,3-dialkoxyprop-1-yne is required for each equivalent of acetimidoyl chloride, it is often convenient to use an excess of the 3,3-dialkoxyprop-1-yne, typically a 10 to 20% excess. Similarly, a 10 to 20% molar excess of alkali metal iodide and alkali metal phosphate are generally preferred. While the reaction is catalytic in copper (I) iodide, usually about 0.1 to about 0.3 equivalents are employed. The coupling reaction is conducted in a polar aprotic solvent at a temperature from about 40° C. to about 100° C. Preferred polar aprotic solvents include ethers like tetrahydrofuran, esters like ethyl acetate, nitriles like acetonitrile, amides like N,N-dimethylformamide and N-methylpyrrolidinone and sulfoxides like dimethyl sulfoxide. Anhydrous solvents are preferred with anhydrous acetonitrile being especially preferred.

In a typical reaction, 2,2,2-trifluoro-N-(4-methoxyphenyl) acetimidoyl chloride and a slight excess of 3,3-diethoxyprop-1-yne are mixed with about 0.3 equivalents of copper (I) iodide and slight excesses of potassium phosphate and potassium iodide in anhydrous acetonitrile. The mixture is heated at about 60° C. under a nitrogen atmosphere until the reaction is complete. After cooling, an extraction solvent like a halogenated hydrocarbon is added to the mixture along with water. The organic layer is recovered, washed with brine and dried. The solvent is evaporated to provide crude N-(5,5-diethoxy-1,1,1-trifluoro-pent-3-yn-2-ylidene)-4-methoxyaniline.

In step c), the N-(5,5-diethoxy-1,1,1-trifluoro-pent-3-yn-2-ylidene)-4-methoxyaniline is reacted with a methylene amine substituted with an alkyl, cyclopropyl, alkenyl or (substituted)phenyl group in the presence of an inorganic alkali metal base in a polar aprotic solvent to produce a 4-(4-methoxyphenyl)amino-5-fluoro-6-(substituted)pyridine-2-dialkyl acetal. While one equivalent of substituted methylene amine is required for each equivalent of N-(5,5-diethoxy-1,1,1-trifluoro-pent-3-yn-2-ylidene)-4-methoxyaniline, it is often convenient to use an excess of the substituted methylene amine, typically a 2 to 4 fold excess. Suitable inorganic alkali metal bases include the lithium, sodium, potassium and cesium salts of hydroxides, carbonates and phosphates. Cesium carbonate is particularly preferred. In general, it is convenient to use a 2 to 4 fold excess of the inorganic alkali metal base. Preferred polar aprotic solvents include ethers like tetrahydrofuran, esters like ethyl acetate, nitriles like acetonitrile, amides like N,N-dimethylformamide and N-methylpyrrolidinone and sulfoxides like dimethyl sulfoxide. Anhydrous solvents are preferred with anhydrous tetrahydrofuran and dimethyl sulfoxide being especially preferred. The reaction is typically conducted at a temperature from about ambient to about 100° C.

In a typical reaction, N-(5,5-diethoxy-1,1,1-trifluoro-pent-3-yn-2-ylidene)-4-methoxyaniline is mixed with about a 2.5 to 3 fold excess of p-chlorobenzylamine and about a 2.5 to 3 fold excess of cesium carbonate in anhydrous tetrahydrofuran. The mixture is heated at about 80° C. until the reaction is complete. After cooling, an extraction solvent like a halogenated hydrocarbon is added to the mixture along with water. The organic layer is recovered, washed with brine and dried. The solvent is evaporated to provide crude 2-(4-chlorophenyl)-6-(diethoxymethyl)-3-fluoro-N-(4-methoxyphenyl)pyridin-4-amine.

In step d), the 4-(4-methoxyphenyl)amino-5-fluoro-6-(substituted)pyridine-2-dialkyl acetal is chlorinated with 1,3-dichloro-5,5-dimethylimidazolidine-2,4-dione in a polar solvent at a temperature from about ambient to about 100° C. to produce 4-((3-chloro-6-(substituted)-2-(dialkoxymethyl)-5-fluoropyridin-4-yl)imino)cyclohexa-2,5-dienone. While one equivalent of 1,3-dichloro-5,5-dimethyl-imidazolidine-2,4-dione is required for each equivalent of 4-(4-methoxyphenyl) amino-5-fluoro-6-(substituted)pyridine-2-dialkyl acetal, it is often convenient to use an excess of the 1,3-dichloro-5,5-dimethylimidazolidine-2,4-dione, typically a 2 to 4 fold excess. The chlorination is conveniently performed in a mixture of a polar solvent such as acetonitrile with water.

In a typical reaction, crude 2-(4-chlorophenyl)-6-(diethoxymethyl)-3-fluoro-N-(4-methoxyphenyl)pyridin-4-amine is treated with two equivalents of 1,3-dichloro-5,5-dimethylimidazolidine-2,4-dione in an acetonitrile/water mixture. The mixture is stirred at ambient temperature until the reaction is complete. The solid product is collected by filtration, washed with additional acetonitrile/water mixture and dried, providing crude 4-((3-chloro-6-(4-chlorophenyl)-2-(diethoxymethyl)-5-fluoropyridin-4-yl)imino)cyclohexa-2,5-dienone.

In step e), the 4-((3-chloro-6-(substituted)-2-(dialkoxymethyl)-5-fluoropyridin-4-yl)imino)cyclohexa-2,5-dienone is treated with a mineral acid in a polar solvent at a temperature from about ambient to about 100° C. to produce a 4-amino-5-fluoro-3-chloro-6-(substituted)picolinaldehyde. Suitable mineral acids include sulfuric and phosphoric acids with sulfuric acid being preferred. The mineral acids are usually used as aqueous solutions. Approximately one equivalent of mineral acid is required but a 10 to 30% excess is preferred. The deprotection/hydrolysis is conveniently performed in a mixture of a polar solvent such as acetonitrile with water.

In a typical reaction, 4-((3-chloro-6-(4-chlorophenyl)-2-(diethoxymethyl)-5-fluoropyridin-4-yl)imino)cyclohexa-2,5-dienone is treated with a 1 M (molar) solution of sulfuric acid in a mixture of acetonitrile/water. The mixture is heated at reflux until the reaction is complete. The mixture is added to methylene chloride, and the organic layer is separated, washed with brine and dried. The solvent is evaporated to provide crude 4-amino-3-chloro-6-(4-chlorophenyl)-5-fluoropicolinaldehyde.

In step f), the 4-amino-5-fluoro-3-chloro-6-(substituted) picolinaldehyde is oxidized with an alkali metal chlorite in the presence of an inorganic acid and a hypochlorous acid scavenger in an aqueous alcoholic solvent to produce a 4-amino-5-fluoro-3-chloro-6-(substituted)picolinic acid. While one equivalent of sodium chlorite is required for the oxidation of the aldehyde to the carboxylic acid, it is often convenient to use 2-8 equivalents. The oxidation occurs in mixtures of water with organic solvents such as acetonitrile or t-butyl alcohol under slightly acidic conditions (pH 3-5), achieved by the addition of 2-10 equivalents of inorganic acid salts such as disodium hydrogen phosphate. To avoid unwanted reactions from the hypochlorous acid formed during the oxidation, 2-30 equivalents of a scavenger such as 2-methyl-2-butene, resorcinol or sulfamic acid is added.

In a typical reaction, 4-amino-3-chloro-6-(4-chlorophenyl)-5-fluoropicolinaldehyde is oxidized with an excess of sodium chlorite, between 20-30 equivalents of 2-methyl-2-butene and about 5 equivalents of disodium hydrogen phosphate in a t-butyl alcohol/water mixture. The mixture is heated at about 80° C. until the reaction is complete. After cooling, the mixture is treated with dilute hydrochloric acid and extracted with ethyl acetate. The organic layer is separated and dried. The solvent is evaporated to provide crude 4-amino-3-chloro-6-(4-chlorophenyl)-5-fluoropicolinic acid.

In step g), the 4-amino-5-fluoro-3-chloro-6-(substituted) picolinic acid is esterified. Esters of the picolinic acids are prepared by coupling of picolinic acid with an alcohol using any number of suitable activating agents such as those used for peptide couplings such as dicyclohexylcarbodiimide (DCC) or carbonyl diimidazole (CDI) or by reacting the corresponding acid with an appropriate arylalkyl alcohol in the presence of an acid catalyst. Alternatively, the esters can be prepared by reacting the picolinic acid with an alkyl or arylalkyl halide in the presence of a base. These procedures are well known to organic chemists and are described, for example, in U.S. Patent Application Publication 2012/0190551 A1.

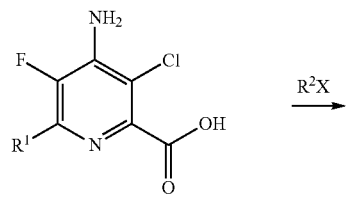

$R^2X$ →

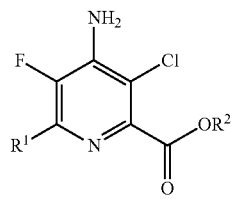

In a typical reaction, 4-amino-3-chloro-6-(4-chlorophenyl)-5-fluoropicolinic acid is reacted with a slight excess of benzyl bromide and about 2 equivalents of potassium carbonate in a polar aprotic solvent such as dimethyl sulfoxide or N,N-dimethylformamide. Benzyl 4-amino-3-chloro-6-(4-chlorophenyl)-5-fluoropicolinate is recovered by partitioning the reaction mixture between ethyl acetate and water, separating and drying the organic phase and evaporating the solvent.

The products obtained by any of these processes, can be recovered by conventional means, such as evaporation or extraction, and can be purified by standard procedures, such as by recrystallization or chromatography.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example 1

2,2,2-Trifluoro-N-(4-methoxyphenyl)acetimidoyl chloride

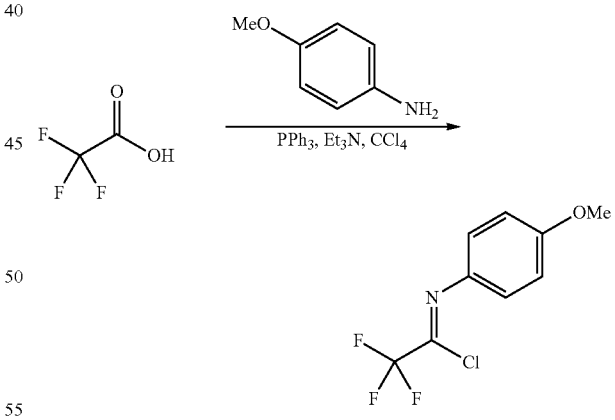

A mixture of triphenylphosphine (34.6 grams (g), 132.0 millimoles (mmol)), 2,2,2-trifluoroacetic acid (3.37 milliliters (mL), 44 mmol), triethylamine (7.38 mL, 53.0 mmol) and carbon tetrachloride (21.33 mL, 220.0 mmol) was magnetically stirred while cooled with an ice bath. After 10 minutes (min), p-methoxyaniline (6.53 g, 53.0 mmol) dissolved in carbon tetrachloride (21.33 mL, 220.0 mmol) was added slowly (exothermic). The ice bath was removed and the reaction mixture was stirred at reflux for 4 hours (h). Upon cooling to room temperature, the reaction mixture was washed with hexane (3×100 mL). Solvent was removed using a rotary evaporator to give 9.8 g of an orange oil. Distillation gave 2,2,2-trifluoro-N-(4-methoxyphenyl)acetimidoyl chloride (9.31 g, 39.2 mmol, 89% yield) as a light yellow liquid: by 75-77° C./0.3 mmHg; $^1$H NMR (400 MHz, CDCl$_3$) δ 7.31 (m, 2H), 6.96 (m, 2H), 3.84 (s, 3H); $^{13}$C NMR (101 MHz, CDCl$_3$) δ 159.56 (s), 135.45 (s), 127.98 (q), 124.35 (s), 117.05 (q), 114.25 (s), 55.50 (s).

Example 2

N-(5,5-Diethoxy-1,1,1-trifluoropent-3-yn-2-ylidene)-4-methoxyaniline

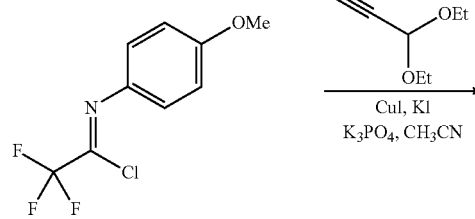

To a magnetically stirred solution of 2,2,2-trifluoro-N-(4-methoxyphenyl)-acetimidoyl chloride (2.376 g, 10.00 mmol) and 3,3-diethoxyprop-1-yne (1.538 g, 12.00 mmol) in acetonitrile (20 mL) was added a ground-up mixture of copper(I) iodide (0.571 g, 3.00 mmol), potassium phosphate (2.55 g, 12.0 mmol) and potassium iodide (1.660 g, 10.00 mmol). After heating under nitrogen at 60° C. for 16 h, the reaction mixture was added to methylene chloride (CH$_2$Cl$_2$; 100 mL) and water (50 mL). The organic layer was washed with a saturated solution of sodium chloride (NaCl) and dried (magnesium sulfate; MgSO$_4$), and the solvent was removed leaving 3.35 g of a yellow liquid. Flash chromatography on silica gel eluting with 5% ethyl acetate (EtOAc)/hexane gave N-(5,5-diethoxy-1,1,1-trifluoropent-3-yn-2-ylidene)-4-methoxyaniline (2.75 g, 8.18 mmol, 82% yield) as a yellow liquid: $^1$H NMR (400 MHz, CDCl$_3$) δ 7.46 (m, 2H), 6.93 (m, 2H), 5.41 (s, 1H), 3.84 (s, 3H), 3.63 (m, 4H), 1.22 (m, 6H); $^{13}$C NMR (101 MHz, CDCl$_3$) δ 160.00 (s), 139.55 (s), 134.98 (s), 134.59 (s), 124.65 (s), 113.98 (s), 94.64 (s), 91.21 (s), 74.83 (s), 61.55 (s), 55.50 (s), 15.00 (s); $^{19}$F NMR (376 MHz, CDCl$_3$) δ −70.91 (s); HRMS-ESI (m/z) [M+H]$^+$ calcd for C$_{16}$H$_{18}$F$_3$NO$_3$, 329.1239; found, 329.1225.

Example 3

2-(4-Chlorophenyl)-6-(diethoxymethyl)-3-fluoro-N-(4-methoxyphenyl)pyridin-4-amine

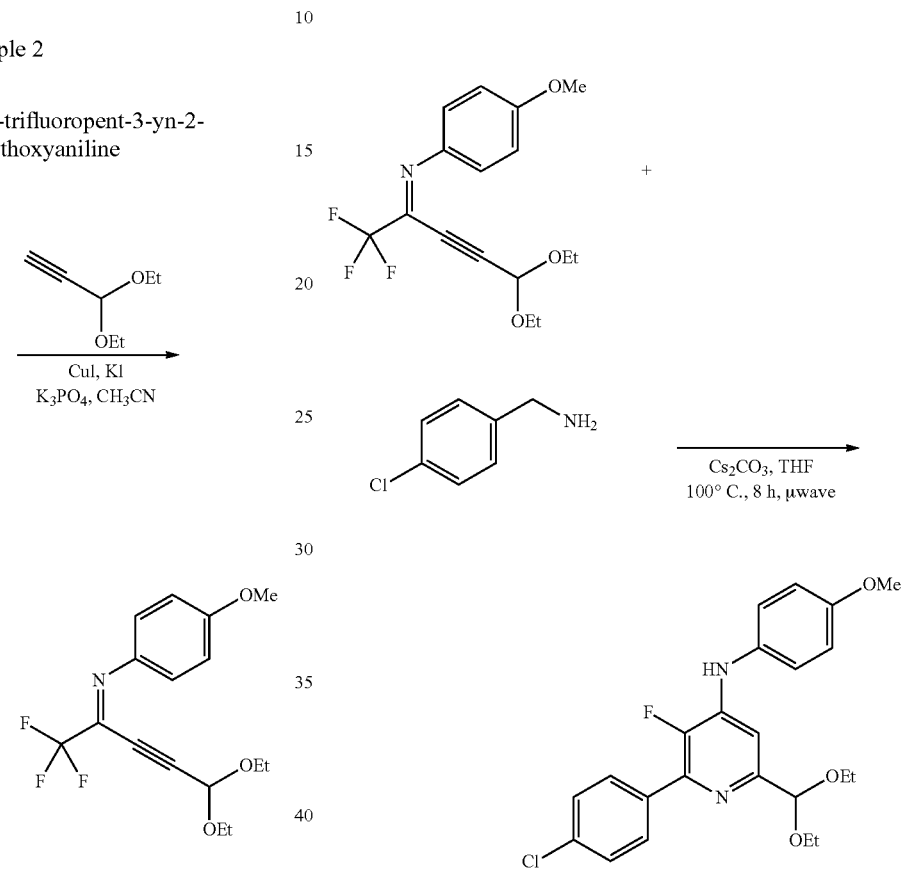

A magnetically stirred solution of N-(5,5-diethoxy-1,1,1-trifluoropent-3-yn-2-ylidene)-4-methoxyaniline (0.659 g, 2 mmol), p-chlorobenzyl amine (0.850 g, 6.00 mmol) and cesium carbonate (1.629 g, 5.00 mmol) in anhydrous tetrahydrofuran (THF; 10 mL) was heated at 100° C. in the microwave for 8 h. The reaction mixture was added to ether (100 mL) and water (50 mL). The organic layer was washed with a saturated solution of NaCl and dried (MgSO$_4$), and the solvent was removed leaving 1.42 g of a yellow solid. Flash chromatography on silica gel eluting with 10% EtOAc/hexane gave 2-(4-chlorophenyl)-6-(diethoxymethyl)-3-fluoro-N-(4-methoxyphenyl)pyridin-4-amine (0.689 g, 1.600 mmol, 80% yield) as an off-white solid: mp 110-111° C.; $^1$H NMR (400 MHz, CDCl$_3$) δ 7.90 (dd, J=8.5, 1.4 Hz, 2H), 7.43 (m, 2H), 7.18 (m, 2H), 7.13 (d, J=6.2 Hz, 1H), 6.94 (m, 2H), 6.19 (d, J=3.7 Hz, 1H), 5.31 (br s, 1H), 3.84 (s, 3H), 3.73 (m, 2H), 3.57 (m, 2H), 1.22 (t, J=7.1 Hz, 6H); $^{19}$F NMR (376 MHz, CDCl$_3$) δ −150.95; HRMS-ESI (m/z) [M+H]$^+$ calcd for C$_{23}$H$_{24}$ClFN$_2$O$_3$, 430.1459; found, 430.1457.

Example 4

4-((3-Chloro-6-(4-chlorophenyl)-2-(diethoxymethyl)-5-fluoropyridin-4-yl)imino)cyclohexa-2,5-dienone

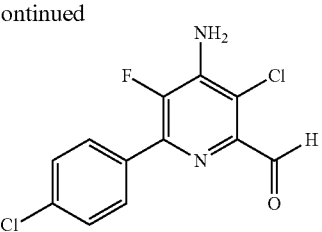

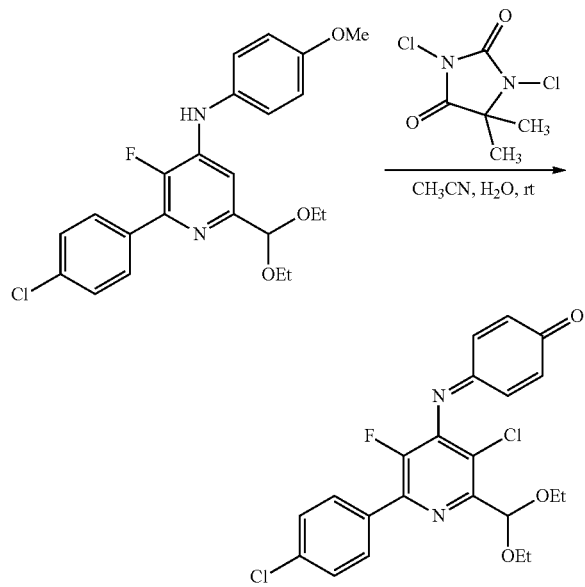

A mixture of 2-(4-chlorophenyl)-6-(diethoxymethyl)-3-fluoro-N-(4-methoxy-phenyl)pyridin-4-amine (0.862 g, 2 mmol) and 1,3-dichloro-5,5-dimethylimidazolidine-2,4-dione (0.788 g, 4.00 mmol) in 1:1 acetonitrile/water (20 mL) was stirred at room temperature. After 2 h, the orange solid was collected by filtration, washed with 1:1 acetonitrile/water (5 mL), dried at room temperature and recrystallized from ether/hexane. 4-((3-Chloro-6-(4-chlorophenyl)-2-(diethoxymethyl)-5-fluoropyridin-4-yl)imino)cyclohexa-2,5-dienone (0.272 g, 30% yield) was isolated as orange crystals: mp 134-136° C.; $^1$H NMR (400 MHz, CDCl$_3$) δ 7.96 (m, 2H), 7.44 (m, 3H), 6.76 (m, 2H), 6.58 (dd, J=10.2, 2.1 Hz, 1H), 5.79 (s, 1H), 3.90 (m, 2H), 3.72 (m, 2H), 1.31 (t, J=7.1 Hz, 6H); $^{19}$F NMR (376 MHz, CDCl$_3$) δ −134.18; HRMS-ESI (m/z) [M+H]$^+$ calcd for C$_{22}$H$_{19}$Cl$_2$FN$_2$O$_3$, 448.0757; found, 448.0761.

Example 5

4-Amino-3-chloro-6-(4-chlorophenyl)-5-fluoropicolinaldehyde

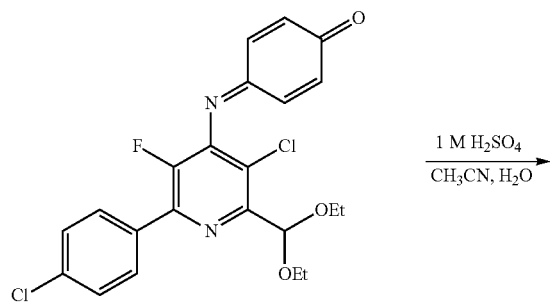

A mixture of 4-((3-chloro-6-(4-chlorophenyl)-2-(diethoxymethyl)-5-fluoropyridin-4-yl)imino)cyclohexa-2,5-dienone (180 milligrams (mg), 0.401 mmol) and 0.1 molar (M) sulfuric acid (H$_2$SO$_4$; 0.5 mL) in a 1:1 mixture of acetonitrile/water (4 mL) was heated to 80° C. for 1 h. After stirring at room temperature for 2 h, the reaction mixture was added to CH$_2$Cl$_2$ (20 mL). The organic layer was washed with a saturated solution of NaCl and dried (MgSO$_4$), and the solvent was removed leaving 4-amino-3-chloro-6-(4-chlorophenyl)-5-fluoropicolinaldehyde (82 mg, 0.273 mmol, 68% yield) as an off-white solid: mp 166-169° C.; $^1$H NMR (400 MHz, CDCl$_3$) δ 10.12 (s, 1H), 7.96 (m, 2H), 7.48 (m, 2H), 4.99 (s, 2H); $^{19}$F NMR (376 MHz, CDCl$_3$) δ −137.68; ESIMS m/z 285.64 ([M+H]$^+$).

Example 6

4-Amino-3-chloro-6-(4-chlorophenyl)-5-fluoropicolinic acid

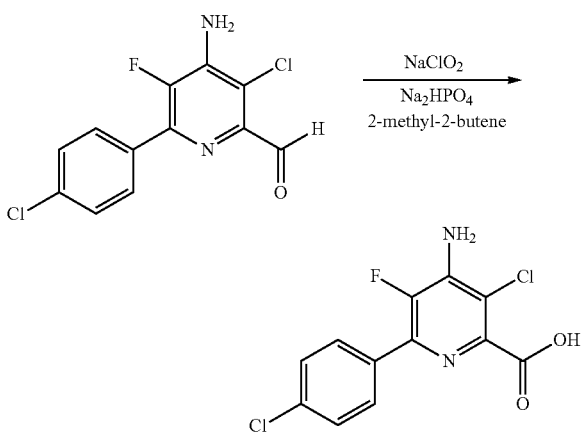

4-Amino-3-chloro-6-(4-chlorophenyl)-5-fluoropicolinaldehyde (105 mg, 0.37 mmol) was dissolved in t-butyl alcohol (2.2 mL). Water (800 μL), 2-methyl-2-butene (1.0 mL, 700 mg, 10 mmol), disodium hydrogen phosphate (Na$_2$HPO$_4$; 276 mg, 2 mmol) and sodium chlorite (106 mg, 1.2 mmol) were added to a crimp seal microwave vial. The reactants were mixed, and the reaction vessel was sealed and heated to 80° C. for 16 h. The reaction mixture was then cooled to ambient temperature, and the mixture was diluted with 1 normal (N) hydrochloric acid (HCl; 5 mL) and EtOAc (10 mL). After stirring for 5 min, the layers were separated, and the aqueous layer was extracted with EtOAc (4×5 mL). The combined organic layers were dried (sodium sulfate; Na₂SO₄) and evaporated to dryness to provide 95 mg of an oily brown solid. The solid was dissolved in a minimum of aqueous 1 N sodium hydroxide (NaOH) and slowly neutralized with aqueous 4 N HCl until a white/brown precipitate appeared. The precipitate was collected and dried, yielding 4-amino-3-chloro-6-(4-chlorophenyl)-5-fluoropicolinic acid (78 mg, 72% yield): $^1$H NMR (400 MHz, CDCl₃) δ 8.5 (br s, 1H), 7.96-7.86 (m, 2H), 7.59-7.75 (m, 2H), 6.1 (br s, 2H); $^{19}$F NMR (376 MHz, DMSO-d₆) δ −141.07; ESIMS m/z 299. 4 ([M−H]⁻).

Example 8

Benzyl 4-amino-3-chloro-6-(4-chlorophenyl)-5-fluoropicolinate

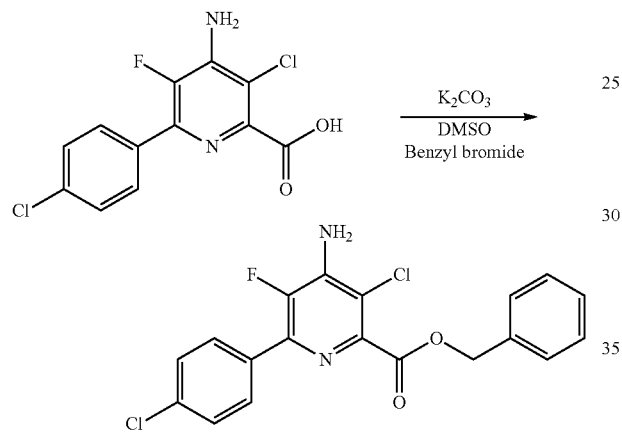

4-Amino-3-chloro-6-(4-chlorophenyl)-5-fluoropicolinic acid (23.1 mg, 0.080 mmol) was dissolved in dimethyl sulfoxide (800 μL) in a crimp seal microwave vial. Potassium carbonate (23.4 mg, 0.166 mmol) was added together with benzyl bromide (10 μL, 14.4 mg, 0.084 mmol). The reaction vessel was sealed and the reaction mixture was vigorously stirred for 16 h at room temperature. The reaction mixture was then partitioned between water (10 mL) and EtOAc (10 mL). The layers were separated, and the aqueous layer was extracted with additional EtOAc (3 mL). The combined organic layers were washed with water (3×4 mL), washed with brine (2 mL), dried (Na₂SO₄) and evaporated to dryness to provide 26.1 mg of white solid. The crude product was purified using flash column chromatography using a 4 g ISCO silica column eluted with a gradient of 0-100% EtOAc/hexanes over 16 min. The crude product was loaded on the column with a minimum amount of methylene chloride. Benzyl 4-amino-3-chloro-6-(4-chlorophenyl)-5-fluoro-picolinate (8.3 mg, 25% yield) was obtained as a light waxy oil: $^1$H NMR (400 MHz, CDCl₃) δ 7.93-7.91 (s, J=7.3 Hz, 2H), 7.53-7.35 (m, 7H), 5.46 (s, 2H), 4.94-4.87 (br m, 2H); $^{19}$F NMR (376 MHz, DMSO) δ −144.88; ESIMS m/z 391. 4 ([M+H]⁺).

What is claimed is:

1. A process for the preparation of a 4-amino-5-fluoro-3-chloro-6-(substituted)picolinate of the Formula I

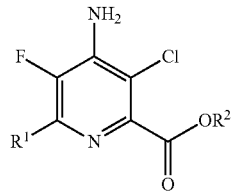

I wherein
R¹ represents C₁-C₄ alkyl, cyclopropyl, C₂-C₄ alkenyl or phenyl substituted with from 1 to 4 substituents independently selected from halogen, C₁-C₄ alkyl, C₁-C₄ haloalkyl, C₁-C₄ alkoxy or C₁-C₄ haloalkoxy, and
R² represents C₁-C₁₂ alkyl or an unsubstituted or substituted C₇-C₁₁ arylalkyl, which comprises the following steps:
a) contacting trifluoroacetic acid with p-methoxyaniline in the presence of a triarylphosphine and a trialkylamine base in carbon tetrachloride solvent to produce an acetimidoyl chloride of Formula A

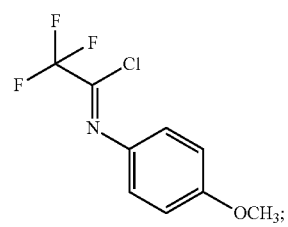

A b) contacting the acetimidoyl chloride of Formula A with a 3,3-dialkoxyprop-1-yne (Formula B)

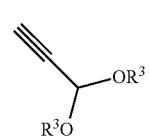

B wherein R³ represents C₁-C₄ alkyl,
in the presence of copper (I) iodide, an alkali metal iodide and an alkali metal phosphate in a polar aprotic solvent to produce an (imino)pent-2-yne dialkyl acetal of Formula C

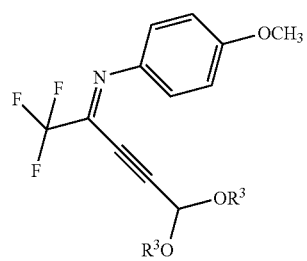

C wherein R³ is as previously defined;

c) cyclizing the (imino)pent-2-yne dialkyl acetal of Formula C with an amine of Formula D

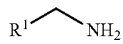
D wherein R¹ is as previously defined,
in the presence of an inorganic alkali metal base in a polar aprotic solvent at a temperature from about ambient to about 100° C. to produce a 4-(4-methoxyphenyl)amino-5-fluoro-6-(substituted)pyridine-2-dialkyl acetal of Formula E

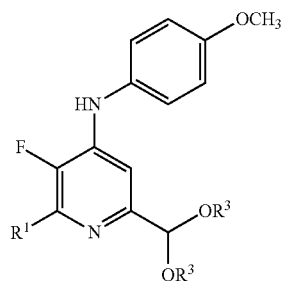
E wherein R¹ and R³ are as previously defined;

d) chlorinating the 4-(4-methoxyphenyl)amino-5-fluoro-6-(substituted)pyridine-2-dialkyl acetal of Formula E with 1,3-dichloro-5,5-dimethylimidazolidine-2,4-dione (Formula F)

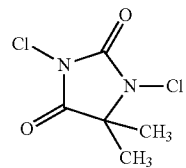
F in a polar solvent to produce the protected 4-amino-5-fluoro-3-chloro-6-(substituted)pyridine-2-dialkyl acetal of the Formula G

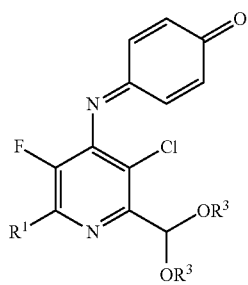
G wherein R¹ and R³ are as previously defined;

e) deprotecting and hydrolyzing the protected 4-amino-5-fluoro-3-chloro-6-(substituted) pyridine-2-dialkyl acetal of the Formula G with a mineral acid in a polar solvent to produce the 4-amino-5-fluoro-3-chloro-6-(substituted)picolinaldehyde of the Formula H

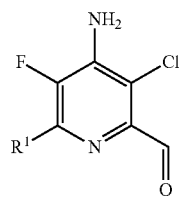
H wherein R¹ is as previously defined;

f) oxidizing the 4-amino-5-fluoro-3-chloro-6-(substituted) picolinaldehyde of the Formula H with an alkali metal chlorite in the presence of an inorganic acid and a hypochlorous acid scavenger in an aqueous alcoholic solvent to produce a 4-amino-5-fluoro-3-chloro-6-(substituted)picolinic acid of the Formula J

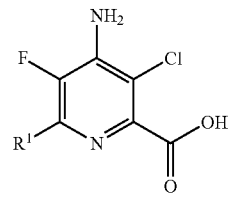
J wherein R¹ is as previously defined; and g) esterifying the 4-amino-5-fluoro-3-chloro-6-(substituted)picolinic acid of the Formula J with a compound of the formula

R²X wherein

X represents OH, Cl, Br, or I, and

R² is as previously defined, to produce a 4-amino-5-fluoro-3-chloro-6-(substituted)picolinate of Formula I.

* * * * *